(12) United States Patent
Iwasaki et al.

(10) Patent No.: US 7,951,074 B2
(45) Date of Patent: May 31, 2011

(54) ENDOSCOPE DEVICE

(75) Inventors: Tomoki Iwasaki, Hino (JP); Tsutomu Hirai, Sagamihara (JP); Yutaka Fujisawa, Hachioji (JP); Akihito Kawamura, Tokyo (JP); Akihiko Mochida, Hachioji (JP); Shoichi Amano, Hachioji (JP); Kotaro Ogasawara, Tokyo (JP); Katsuyuki Saito, Sagamihara (JP); Susumu Hashimoto, Hachioji (JP); Makoto Tsunakawa, Toda (JP); Takehiro Nakagawa, Hachioji (JP)

(73) Assignee: Olympus Corporation, Tokyo (JP)

( * ) Notice: Subject to any disclaimer, the term of this patent is extended or adjusted under 35 U.S.C. 154(b) by 1161 days.

(21) Appl. No.: 11/698,963

(22) Filed: Jan. 26, 2007

(65) Prior Publication Data

US 2007/0123749 A1    May 31, 2007

Related U.S. Application Data

(63) Continuation of application No. PCT/JP2005/013725, filed on Jul. 27, 2005.

(30) Foreign Application Priority Data

Jul. 29, 2004    (JP) ................................. 2004-222353

(51) Int. Cl.
*A61B 1/06*    (2006.01)
*A61B 1/00*    (2006.01)

(52) U.S. Cl. .......................... 600/160; 600/101; 600/180

(58) Field of Classification Search .................. 600/101, 600/103, 118, 126

See application file for complete search history.

(56) References Cited

U.S. PATENT DOCUMENTS

| | | | |
|---|---|---|---|
| 5,022,382 A | 6/1991 | Ohshoji et al. | |
| 5,243,967 A * | 9/1993 | Hibino | 600/109 |
| 5,609,563 A * | 3/1997 | Suzuki et al. | 600/118 |
| 5,840,024 A | 11/1998 | Taniguchi et al. | |
| 5,899,852 A * | 5/1999 | Takahashi et al. | 600/118 |
| 6,120,435 A * | 9/2000 | Eino | 600/118 |
| 6,602,186 B1 * | 8/2003 | Sugimoto et al. | 600/126 |
| 7,060,027 B2 * | 6/2006 | Maeda et al. | 600/150 |
| 2002/0033882 A1 | 3/2002 | Wada et al. | |
| 2003/0043264 A1 | 3/2003 | Furuya et al. | |
| 2004/0193014 A1* | 9/2004 | Miyagi et al. | 600/146 |
| 2005/0215857 A1* | 9/2005 | Iwasaki | 600/118 |

FOREIGN PATENT DOCUMENTS

| | | |
|---|---|---|
| EP | 0 025 967 A1 | 4/1981 |
| JP | 11-164812 | 6/1999 |
| JP | 2000-139947 | 5/2000 |
| JP | 2000-189380 | 7/2000 |
| JP | 2001-128992 | 5/2001 |
| JP | 2002-253497 | 9/2002 |
| JP | 2003-070730 | 3/2003 |

* cited by examiner

*Primary Examiner* — Philip R Smith
(74) *Attorney, Agent, or Firm* — Scully, Scott, Murphy & Presser, P.C.

(57) ABSTRACT

An endoscope device is proposed for dealing with an erroneous operation of a surgeon. An endoscope device has an endoscope and a processor, wherein the endoscope has a switch unit and the processor has a CPU and an operating panel. In the event that the CPU of the processor detects that, of a first instruction signal transmitted from the switch unit and a second instruction signal transmitted from the operating panel, the instructions for performing the predetermined operation are not performed normally with one of the instruction signals, and instructions for performing an operation other than the predetermined operation is performed normally with the other instruction signal, the CPU stops the transmission of one of the instruction signals, and validates the operation content instructed by the other instruction signal.

12 Claims, 7 Drawing Sheets

ENDOSCOPE DEVICE

CROSS REFERENCE TO RELATED APPLICATION

This application is a continuation application of PCT/JP2005/013725 filed on Jul. 27, 2005 and claims benefit of Japanese Application No. 2004-222353 filed in Japan on Jul. 29, 2004, the entire contents of which are incorporated herein by this reference.

BACKGROUND OF THE INVENTION

1. Field of the Invention

The present invention relates to an endoscope device, and particularly relates to an endoscope device wherein, in the event that an operation which is not a desired operation is performed, such endoscope device is controlled so as to not perform this operation which is not a desired operation.

2. Description of the Related Art

In general, endoscope devices are widely used in medical fields and so forth. The operational content regarding which a surgeon uses an endoscope device has in recent years become more varied and more complicated, as the content of surgery and testing and so forth on subjects has improved. Therefore, it is necessary to have endoscope devices which can perform operations easily and safely in the case of a surgeon performing surgery and testing and so forth on a subject.

For example, the endoscope system proposed in Japanese Unexamined Patent Application Publication No. 2000-139947 includes a foot switch and a medical device, thus having a configuration wherein one or multiple medical devices can be operated easily and safely, by the surgeon operating the foot switch.

SUMMARY OF THE INVENTION

An endoscope device according to the present invention is an endoscope device comprising: an endoscope and an endoscope control device for performing predetermined control as to the endoscope; the endoscope including a first operating unit which is provided as one or a plurality of operating devices having a mechanical configuration, and which transmits a first instruction signal for performing predetermined operations as to the endoscope and the endoscope control device; and the endoscope control device including a second operating unit which is provided as one or a plurality of operating devices having a mechanical configuration, and which transmits a second instruction signal for performing predetermined operations as to the endoscope and the endoscope control device; wherein the endoscope control device has a control unit for stopping transmission of one of the instruction signals, in the case that an instruction for performing a predetermined operation with one instruction signal of the first instruction signal and the second instruction signal is detected to be abnormal, and also an instruction for performing an operation other than the predetermined operation is detected to be normal, and also for validating the operation content which the other instruction signal instructs.

An endoscope device according to the present invention is an endoscope device comprising: an endoscope and an endoscope control device for performing predetermined control as to the endoscope; the endoscope including a first operating unit which is provided as one or a plurality of operating devices having a mechanical configuration, and which transmits a first instruction signal for performing predetermined operations as to the endoscope and the endoscope control device; and the endoscope control device including a second operating unit which is provided as one or a plurality of operating devices having a mechanical configuration, and which transmits a second instruction signal for performing predetermined operations as to the endoscope and the endoscope control device; wherein the endoscope control device, in the event that at least one of the first instruction signal and the second instruction signal is detected when the power is turned on for the endoscope and the endoscope control device, invalidates the operating content instructed by the instruction signal.

DETAILED DESCRIPTION OF THE PREFERRED EMBODIMENT(S)

The embodiments of the present invention will be described below with reference to the drawings.

Figure 1:
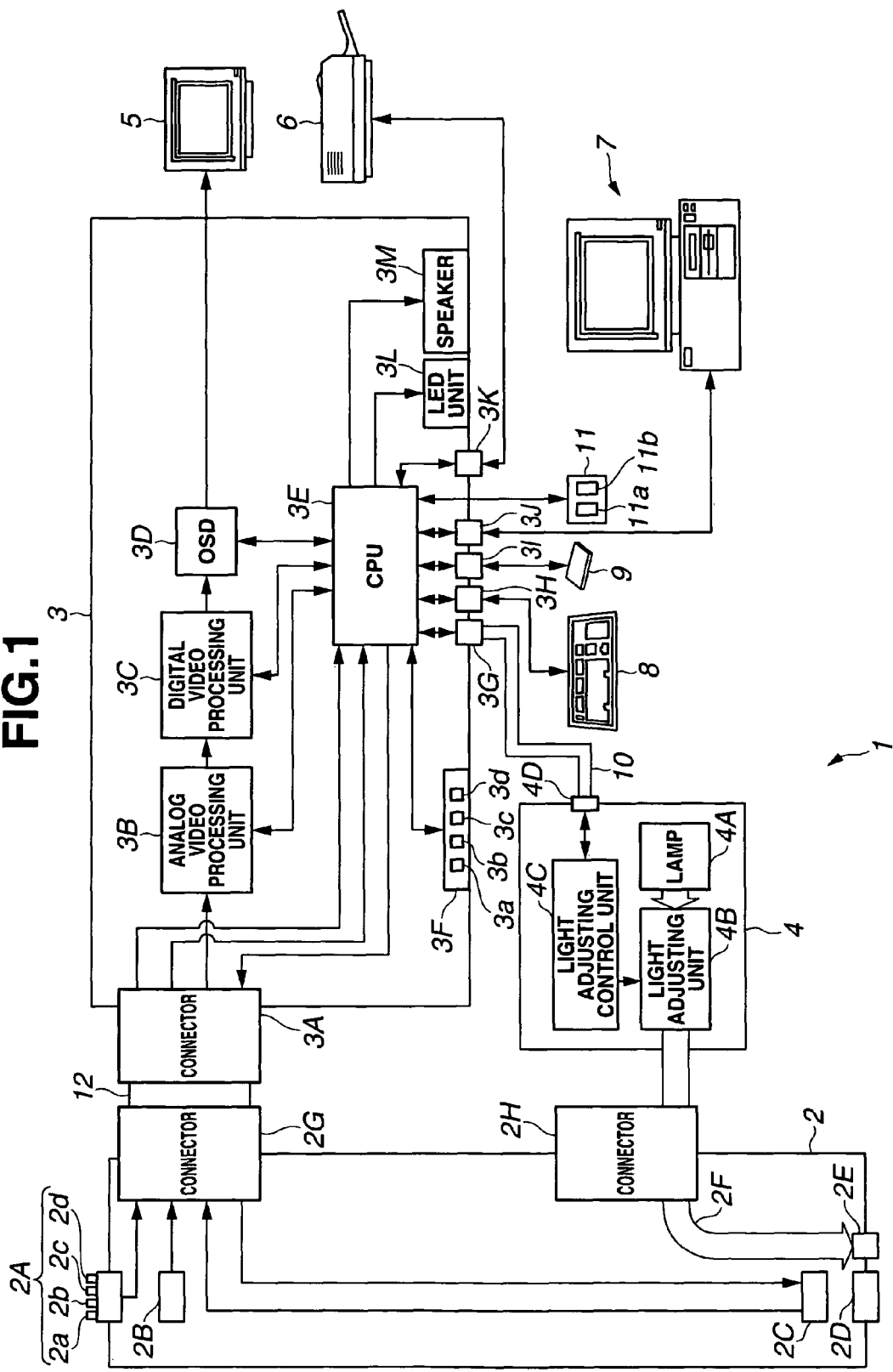
FIG. 1 is a configuration diagram illustrating the entire configuration of an endoscope device according to one embodiment of the present invention.
Figure 2:
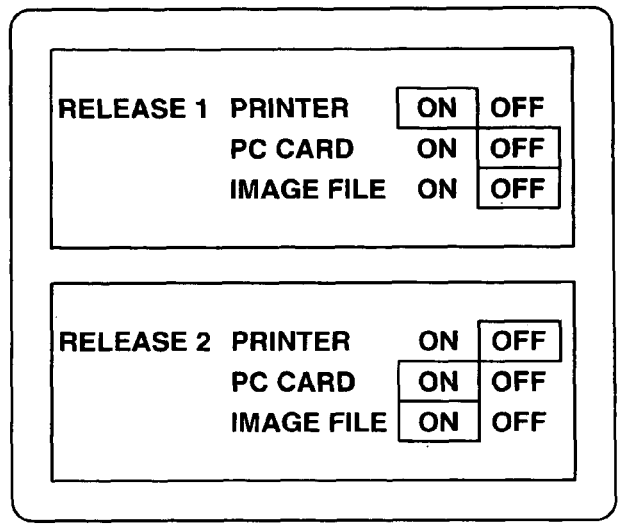
FIG. 2 is a diagram illustrating a screen for setting operation assignments of switches included in the endoscope device according to the present embodiment.
Figure 3:
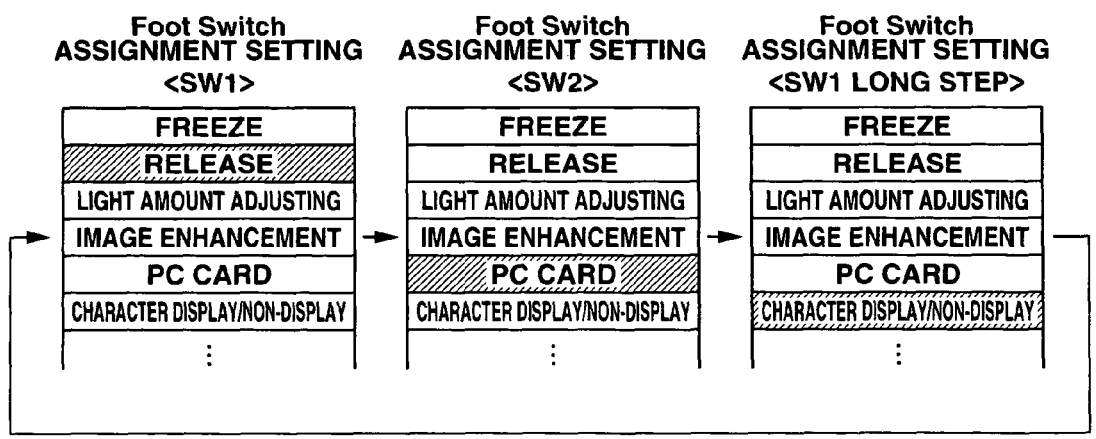
FIG. 3 is a diagram illustrating a screen for setting operation assignments of foot switches included in the endoscope device according to the present embodiment.
Figure 4:
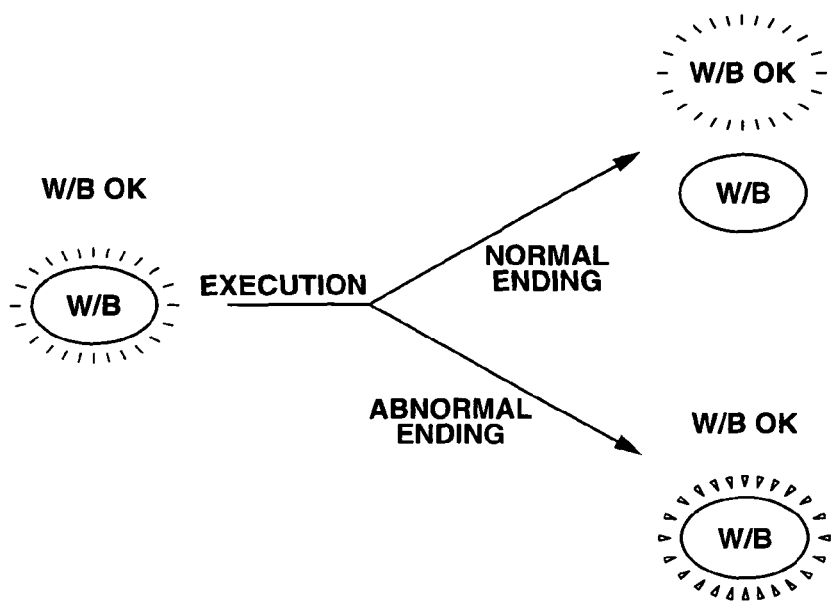
FIG. 4 is a diagram illustrating the operation of a white balance switch included in a processor according to the present embodiment.
Figure 5:
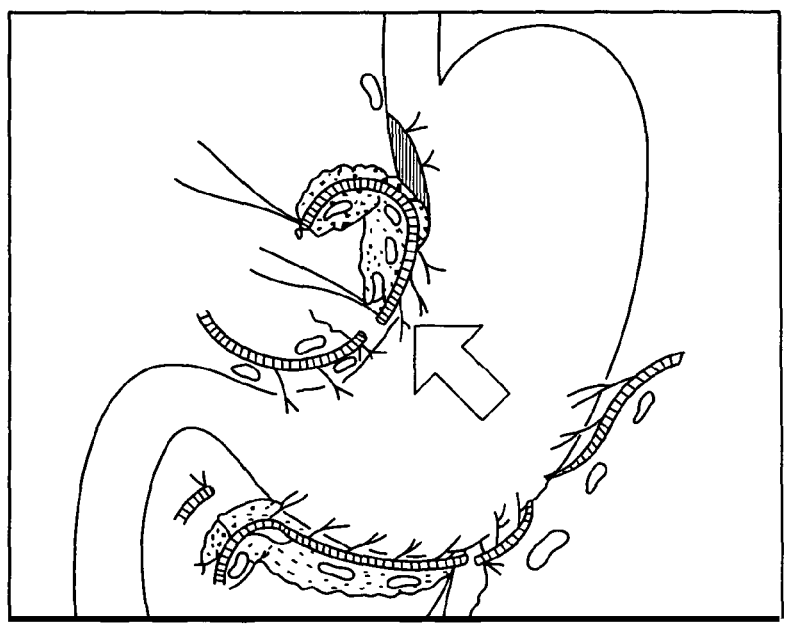
FIG. 5 is a diagram illustrating a pointer displayed on a monitor of the endoscope device according to the present embodiment.
Figure 6:
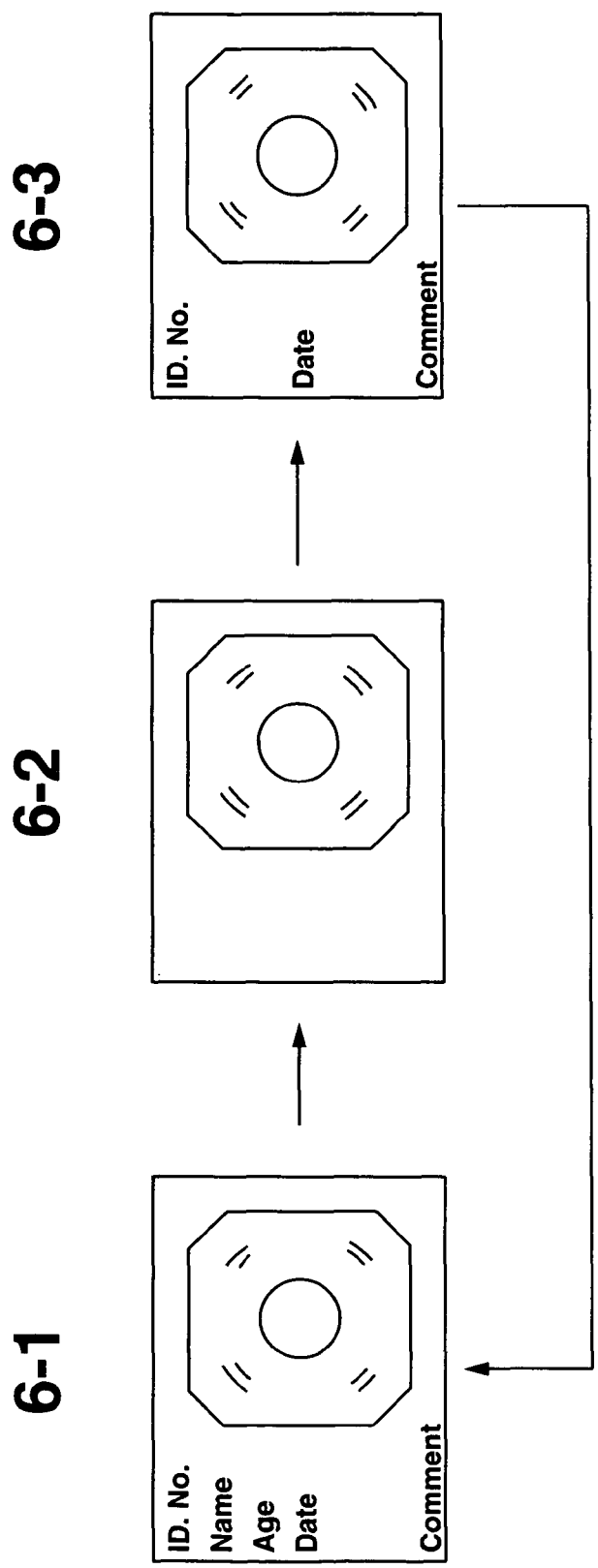
FIG. 6 is a diagram illustrating one example of a screen displayed on a monitor of the endoscope device according to the present embodiment.
Figure 7:
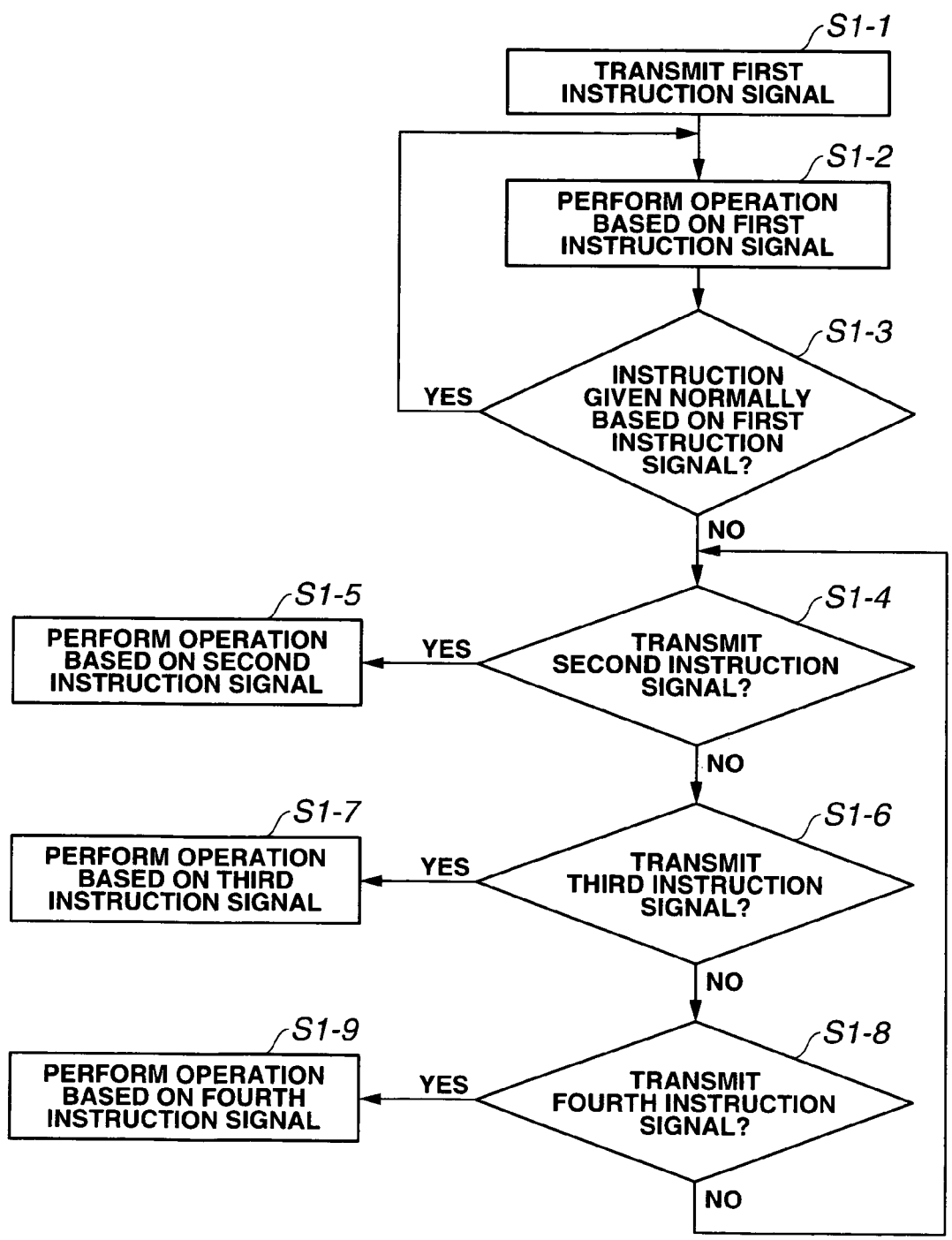
FIG. 7 is a flowchart showing the operations in the event that the processor according to the present embodiment detects an abnormal instruction signal.
Figure 8:
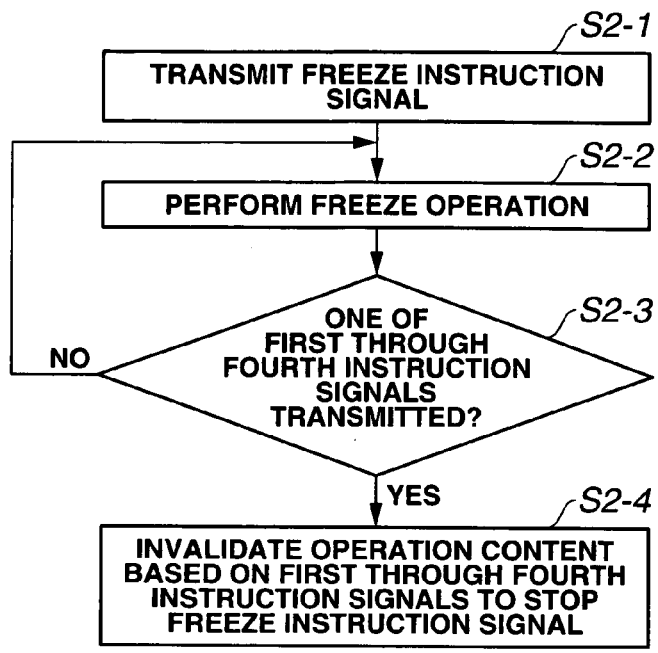
FIG. 8 is a flowchart for the processor according to the present embodiment in the event that a freeze instruction signal is transmitted.
Figure 9:
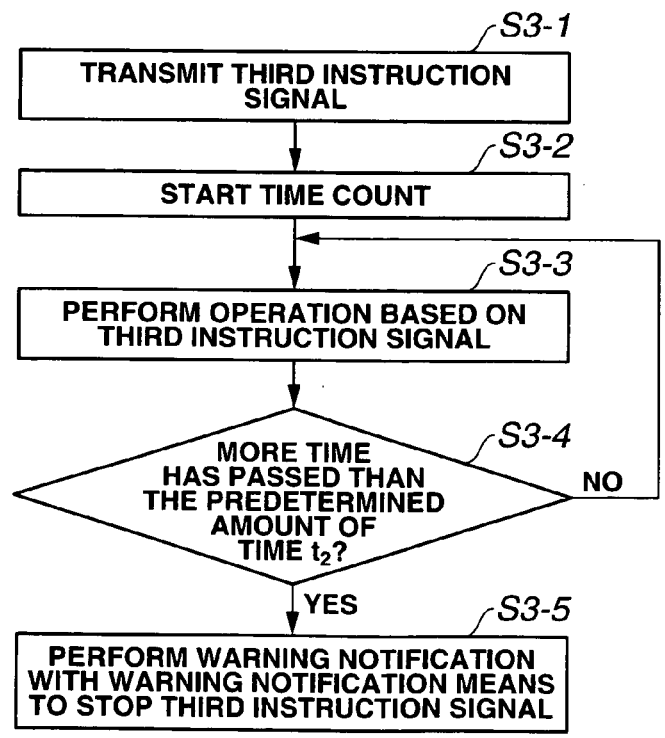
FIG. 9 is a flowchart showing the flow of operations in the event that the processor according to the present embodiment detects a state wherein a third instruction signal is transmitted for a longer time period than a predetermined time period.
Figure 10:
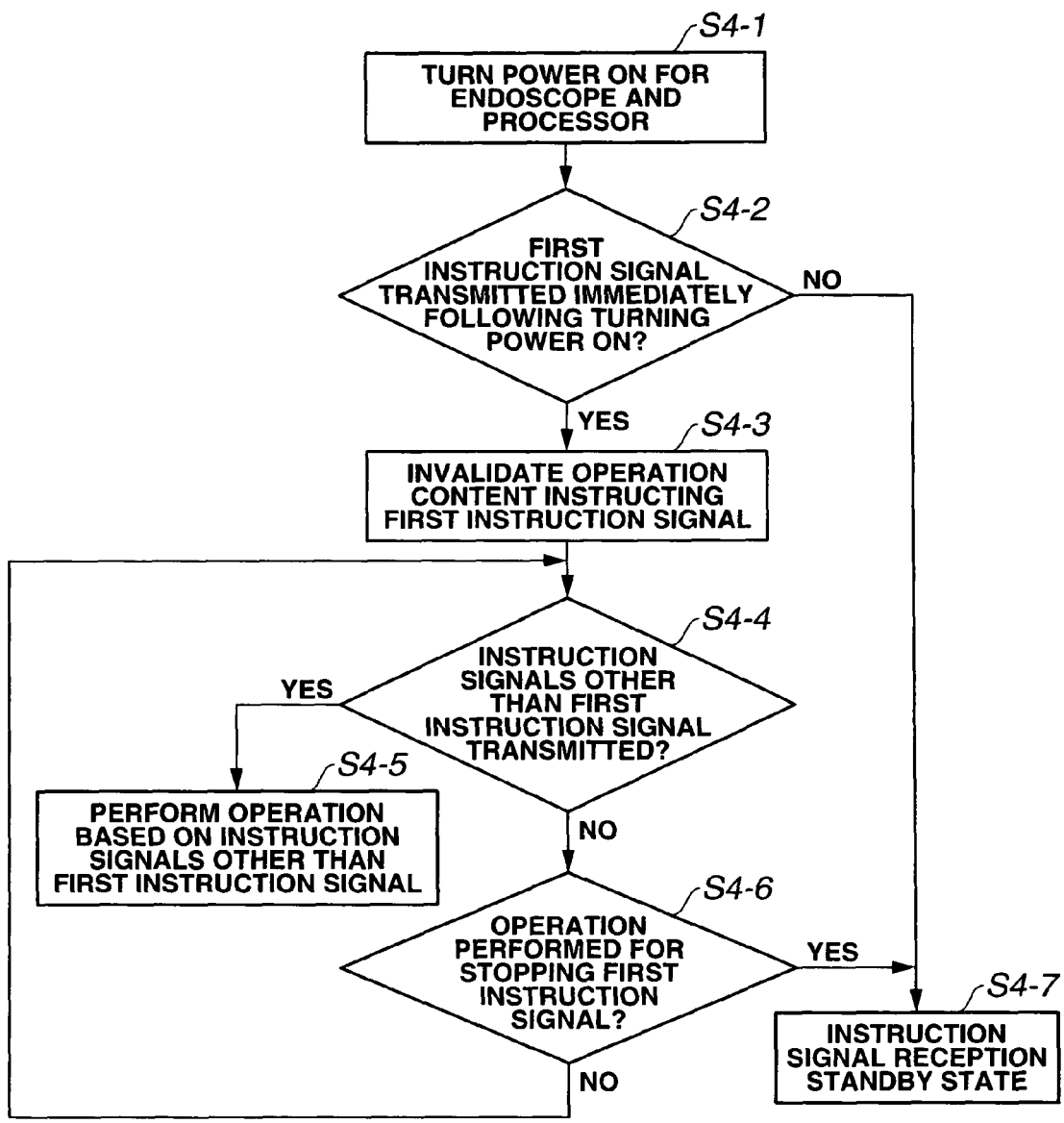
FIG. 10 is a flowchart showing the flow of operations in the event that the processor detects an instruction signal immediately following the power being turned on for the endoscope or the processor according to the present embodiment.

FIG. 1 is a configuration diagram illustrating the entire configuration of an endoscope device according to one embodiment of the present invention. FIG. 2 is a diagram illustrating a screen for setting operation assignments of switches included in the endoscope device according to the present embodiment. FIG. 3 is a diagram illustrating a screen for setting operation assignments of foot switches included in the endoscope device according to the present embodiment. FIG. 4 is a diagram illustrating the operation of a white balance switch included in a processor according to the present embodiment. FIG. 5 is a diagram illustrating a pointer displayed on a monitor of the endoscope device according to the present embodiment. FIG. 6 is a diagram illustrating one example of a screen displayed on a monitor of the endoscope device according to the present embodiment. FIG. 7 is a flowchart showing the flow of operations in the event that the processor according to the present embodiment detects an abnormal instruction signal. FIG. 8 is a flowchart for the processor according to the present embodiment in the event that a freeze instruction signal is transmitted. FIG. 9 is a flowchart showing the flow of operations in the event that the processor according to the present embodiment detects a state wherein a third instruction signal is transmitted for a longer time period than a predetermined time period. FIG. 10 is a flowchart showing the flow of operations in the event that the processor detects an instruction signal immediately following the power being turned on for the endoscope or the processor according to the present embodiment.

As shown in FIG. 1, an endoscope device 1 comprises an endoscope 2, a processor 3 serving as an endoscope control device, a light source device 4, a monitor 5, a printer 6, a terminal device 7, a keyboard 8, a PC card 9, a light adjusting cable 10, a foot switch 11, and a cable 12.

The endoscope 2 has endoscope identifying memory 2B, an image-capturing device 2C which is an image-capturing unit, and a light guide fiber 2F therein. Also, the endoscope 2 has a switch unit 2A serving as a first operating unit, an objective lens 2D, an illumination lens 2E, a connector 2G, and a connector 2H on the external surface thereof.

The endoscope identifying memory 2B may be configured as a non-volatile and rewritable recording unit, for example, wherein equipment type information, individual information and so forth of the endoscope 2 is recorded. Note that the equipment type information, individual information and so forth is transmitted to the processor 3 via the cable 12.

The image-capturing device 2C is provided on an image-forming position of the objective lens 2D, to image-capture a subject, convert the image of the subject which is image-captured into an image signal, and transmits this to the processor 3.

The light guide fiber 2F guides the illumination light supplied from the light source device 4 toward the illumination lens 2E, and illuminates the subject with the guided illumination light.

The connector 2G has a configuration which is detachably attached to the cable 12. Also, the connector 2H has a configuration which is detachable attached to the light guide fiber 2F extending from the exterior surface of the light source device 4.

The switch unit 2A serving as the first operating unit has four switches 2a, 2b, 2c, and 2d service as the operating device, as shown in FIG. 1. By the surgeon performing operation of one of the four switches in the switch unit 2A, for example, instructions, such as freezing instructions which are instructions for temporarily stopping the transmission of an image signal of the image of a subject image-captured by the image-capturing device 2C, or release instructions which are instructions for recording the image signal of the image of the subject image-captured by the image-capturing device 2C as a still image, can be performed as to the endoscope 2 and the processor 3. As for the initializing setting of the switch unit 2A, the switch 2a may have a function for performing the freeze instructions, the switch 2b may have a function performing instructions for light amount adjusting of the illumination light supplied from the light source device 4, the switch 2c may have a function for performing instructions for enhancing processing as to the image signal, and switch 2d may have a function for performing release instructions, may be given as setting examples.

Note that the functional settings of the four switches belonging to the switch unit 2A are changeable by the operations of the terminal device 7 and so forth. For example, a configuration may be set wherein multiple switches having functionality for performing similar instructions can be provided, such as, of the four switches belonging to the switching unit 2A, for example the two switches switch 2a and switch 2b have functionality for performing freezing instructions.

Also, recording a still image by the release instructions can be performed as to the printer 6, the terminal device 7, and the PC card 9. Further, a setting screen such as that shown in FIG. 2 can be displayed on the monitor 5 by the operations by the terminal device 7 and so forth, thus enabling selection of one or multiple devices to be the recording subject for each switch set so as to perform release instructions.

Also, the each of the four switches 2a, 2b, 2c, and 2d have at least a partial mechanical configuration, and so by the surgeon performing an operation such as pressing, rotating, and so forth, instructions such as the freeze instructions described above can be performed as to the endoscope 2 and the processor 3. Note that the number of switches serving as an operating device which are provided on the switch unit 2A are not limited to four, and an arbitrary number of switches may be provided.

The processor 3 includes an analog video processing unit 3B, a digital video processing unit 3C, an OSD (on-screen display) 3D, and a CPU (central processing unit) 3E serving as a control unit therewithin. Also, the processor 3 includes a connector 3A, an operating panel 3F serving as a second operating unit, a connector 3G, a keyboard controller 3H, a PC card slot 3I, a connector 3J, a connector 3K, an LED unit 3L, and a speaker 3M on the exterior surface thereof.

The analog video processing unit 3B receives an image signal transmitted from the image-capturing device 2C, and after performing predetermined image processing such as analog/digital conversion as to the image signal, based on the content of the control signal transmitted from the CPU 3E, transmits the image signal after the predetermined image processing has been performed to the digital video processing unit 3C.

The digital video processing unit 3C receives the image signal transmitted from the analog video processing unit 3B, and after performing predetermined image processing such as color correction and so forth on the image signal, transmits the image signal after the predetermined image processing has been performed on the OSD 3D, based on the contents of the control signal transmitted from the CPU 3E.

The OSD 3D receives image signal transmitted from the digital video processing unit 3C, performs predetermined image processing such that the characters and pointer and so forth are displayed so as to be superimposed when the image signal is displayed on the monitor 5, based on the content of the control signal transmitted from the CPU 3E, transmits the image signal after the predetermined image processing has been performed to the monitor 5.

The CPU 3E has an unshown counter for measuring time, and performs predetermined controls as to each portion of the endoscope 2 and processor 3 and so forth, based on the content of the command signal transmitted from the switch unit 2A and so forth.

The connector 3A is configured to be detachably attached to the cable 12, and is connected to the CPU 3E within the processor 3. The connector 3G is configured to be detachably attached to the light-adjusting cable 10, and is connected to the CPU 3E within the processor 3. The connector 3J is configured to be detachably attached to the terminal device 7 and an unshown cable, and is connected to the CPU 3E within the processor 3. The connector 3K is configured to be detachably attached to the printer 6 and an unshown cable, and is connected to the CPU 3E within the processor 3.

The keyboard controller 3H is configured to be detachably attached to the keyboard 8 and transmits the instruction signal transmitted from the keyboard 8 to the CPU 3E, and also transmits the control signal transmitted from the CPU 3E to the keyboard 8. The PC card slot 3I is configured to be detachably attached to the PC card 9, and is connected to the CPU 3E within the processor 3.

The LED unit 3L has one or multiple unshown LEDs, and performs notification of the states and so forth within each unit of the endoscope 2 and processor 3, by performing lighting or flashing and so forth based on the content of the control signal transmitted from the CPU 3E. The speaker 3M performs notification of the states and so forth within each unit of the endoscope 2 and processor 3, by emitting sound based on the content of the control signal transmitted from the CPU 3E.

The operating panel 3F serving as the second operating unit includes four switches 3a, 3b, 3c, and 3d serving as an operating device, as shown in FIG. 1. Also, the four switches belonging to the operating panel 3F are connected to the CPU 3E within the processor 3. Instructions, such as white balance instructions and so forth which are instructions for performing color adjusting of the image signal using predetermined adjustment treatment tools and so forth, can be performed as to the endoscope 2 and processor 3 before the image-capturing device 2C performs image-capturing of an image of the subject, by the surgeon performing an operation of one of the four switches belonging to the operating panel 3F.

Note that the functional settings of the four switches belonging to the operating panel 3F are changeable by operating the terminal device 7 and so forth. A configuration may be set wherein multiple switches having functionality for performing similar instructions can be provided, such as, of the four switches belonging to the operating panel 3F, for example the two switches switch 3a and switch 3b have functionality for performing white balance instructions. Also, settings can be made wherein one of the four switches belonging to the operating panel 3F have the functionality for performing the above-described freeze instructions or the release instruction by the surgeon operating the terminal device 7 and so forth. Further, the settings can be made wherein one of the four switches belonging to the switch unit 2A have the functionality for performing white balance instructions by the surgeon operating the terminal device 7 and so forth.

Also, the each of the four switches 3a, 3b, 3c, and 3d have at least a partial mechanical configuration, and so by the surgeon performing an operation such as pressing, rotating, and so forth, instructions such as the white balance instructions described above can be performed as to the endoscope 2 and the processor 3. Note that the number of switches serving as an operating device which are provided on the operating panel 3F is not limited to four, and an arbitrary number of switches may be provided.

The light source device 4 includes a lamp 4A, a light-adjusting unit 4B, and a light-adjusting control unit 4C therewithin, and also has a connector 4D on the exterior surface thereupon.

The lamp 4A supplies illumination light to the subject via a light-adjusting unit 4B, light guide fiber 2F, and an illumination lens 2E.

The light-adjusting unit 4B has an unshown filter to perform adjustments and so forth of the amount of illumination light supplied from the lamp 4A, based on the light-adjusting control signal transmitted from the light-adjusting control unit 4C.

The light-adjusting control unit 4C transmits a light-adjusting control signal as to the light-adjusting unit 4B to control the light-adjusting unit 4B, based on the content of the control signal transmitted from the CPU 3E via the light-adjusting cable 10.

The connector 4D is configured to be detachably attached to the light-adjusting cable 10, and is connected to the light-adjusting control unit 4C within the light source device 4.

The monitor 5 is connected to the processor 3, receives the image signal transmitted from the processor 3, and performs image display based on the image signal.

The printer 6 is connected to the processor 3, receives the image signal transmitted from the processor 3, and outputs image printing to an unshown medium such as paper, based on the image signal.

The terminal device 7 is a device such as a personal computer or the like, which can change the functional settings belonging to the switch unit 2A, and can perform recording and so forth of an image signal of a subject which the image-capturing device 2C has image-captured.

The PC card 9 serves as a recording unit such as a compact flash (registered trademark) or the like, and is configured to be detachably attached to the PC card slot 3I. Also, the PC card 9 can receive an image signal of an image which the image-capturing device 2C has image-captured in the state wherein the PC card 9 is connected to the PC card slot 3I, and can perform recording and so forth of this image signal.

The light-adjusting cable 10 is configured to be detachably attached to the connector 3G of the processor 3 and the connector 4D of the light source device 4.

The cable 12 is configured to be detachably attached to the connector 2G of the endoscope 2 and the connector 3A of the processor 3.

The foot switch 11 serving as a third operating unit is provided outside of the processor 3, and is connected to the CPU 3E of the processor 3 via an unshown cable. Note that the foot switch 11 can also be connected to the light-adjusting control unit 4C of the light source device 4 via an unshown cable.

Also the foot switch 11 includes two switches 11a and 11b serving as an operating device. By performing an operation of one of the switches 11a and 11b, the surgeon can perform instructions as to the endoscope 2 and processor 3, such as zoom instructions for expanding a portion of a subject image which the image-capturing device 2C has image-captured, and observing this, or moving image recording instructions for recording an image signal of a subject image which the image-capturing device 2C has image-captured, as a moving image.

Note that the functional settings of the switches 11a and 11b are changeable by operating the terminal device 7 and so forth. A configuration may be set wherein two switches having functionality for performing similar instructions together can be provided, such as the two switches 11a and 11b having functionality for performing zooming instructions together. Also, settings can be made wherein the surgeon displays a setting screen such as that shown in FIG. 3 by operating the terminal device 7 and so forth, whereby one of switches 11a and 11b have the functionality for performing the above-described freeze instructions and so forth. Further, the settings can be made wherein one of the four switches belonging to the switch unit 2A or one of the four switches belonging to the operating panel 3F have the functionality for performing zooming instructions or moving image recording instructions, by the surgeon operating the terminal device 7 and so forth.

Also, each of the switches 11a and 11b have at least a partial mechanical configuration, and so by the surgeon performing an operation such as pressing and so forth, instructions such as the zooming instructions described above can be performed as to the endoscope 2 and the processor 3. Note that the number of switches serving as an operating device which are provided on the foot switch 11 are not limited to two, and an arbitrary number of switches may be provided.

The keyboard 8 serving as a fourth operating unit is provided on the outside of the processor 3, and is connected to a keyboard controller 3H of the processor 3 via an unshown cable. Also, the keyboard 8 has an operating device configured with one or multiple switches for performing character input and predetermined operations as to the endoscope 2 and processor 3. Instructions such as character input instructions for performing character input or printing instructions for printing an image signal of a subject image which the image-capturing device 2C has image-captured with the printer 6, for example, can be performed as to the endoscope 2 and processor 3, by the surgeon performing one of the operations of the operating device belonging to the keyboard 8.

Note that the functional settings of the operating device belonging to the keyboard 8 are changeable by operations by the terminal device 7 and so forth, and the settings may be such that the operating device belonging to the keyboard 8 have multiple functions such as a functionality for performing the above-described freeze instruction, for example. Further, settings can be performed such that one of the four switches belonging to the switch unit 2A, the four switches belonging to the operating panel 3F, or the two switches belonging to the foot switch 11 perform printing instructions, by the surgeon operating the terminal device 7 and so forth.

Also, one or multiple switches serving an operating device belonging to the keyboard 8 each have at least a partial mechanical configuration, and can perform instructions such as the above-described zooming instructions and so forth as to the endoscope 2 and the processor 3, by the surgeon performing an operation such as pressing or the like.

Next, the actions of the endoscope device 1 of the present embodiment will be described with reference to FIG. 1 through FIG. 10.

In the event of using the endoscope device 1, the surgeon uses predetermined treatment tools to perform white balance adjusting for adjusting the color of the subject image which is image-captured by the endoscope 2, by operating a white balance switch having the function for performing white balance instructions, which is one of the switches such as switch 3a and so forth provided on the operating panel 3F, by pressing this continuously only for a predetermined time. As shown in FIG. 4, the white balance switch is lit while in the state of white balance adjusting not being performed. After this, in the event that the surgeon performs a long-pressing operation of the white balance switch to complete the white balance adjusting normally, the white balance switch becomes unlit and the "W/B OK" switch provided on the LED unit 3L is lit, as shown in FIG. 4, thus notifying that the white balance adjusting has been completed normally. Also, in the event that white balance adjusting is not completed normally by the surgeon performing long-pressing operation, the white balance switch is lit after flashing for a predetermined length of time, as shown in FIG. 4, thus notifying that the white balance adjusting has not been completed normally.

After performing the above-described white balance adjusting, the surgeon inserts the endoscope 2 into the body cavity of the subject for performing surgery and testing and so forth.

In the event that an image such as that in FIG. 5 is displayed on the monitor 5 after the surgeon inserts the endoscope 2 into the body cavity, an arrow-shaped pointer such as that shown in FIG. 5 can be displayed on the monitor 5, by operating a pointer switch having functionality for performing instruction to display a pointer on the monitor 5, which is one of the switches such as switch 2a, provided to the switch unit 2A. The pointer is displayed in the center portion of the monitor 5 in the initial state which is the state wherein the pointer switch has not been operated even once after the power of the endoscope 2 and the processor 3 is turned on. Also, the pointer can be displayed in a desired position on the monitor 5, for example by the surgeon operating an unshown arrow key or an unshown pointing device provided on the keyboard 8. The pointer is temporarily not displayed in the event that the pointer switch is turned on and also the operations of the keyboard 8 and so forth are not performed for longer than a predetermined length of time while the pointer is displayed in the desired position on the monitor 5. After this, after operations of the keyboard 8 and so forth are performed, the temporarily non-displayed pointer is displayed again in the desired position on the monitor 5. Also, in the state that the pointer is displayed in the desired position on the monitor 5, in the event that the surgeon turns the pointer switch off once, and after the pointer becomes non-displayed, turns on the pointer switch again, the non-displayed pointer is displayed again in the desired position on the monitor 5. Note that the pointer switch can also be provided on the operating panel 3F and so forth serving as an operating unit other than the switch unit 2A, by changing the settings by the operations of the terminal 7 and so forth, similar to the switch having other functionalities such as white balance and so forth.

Also, after the surgeon inserts the endoscope 2 into the body cavity, in the state that an image such as that shown in image 6-1 in FIG. 6 is displayed on the monitor 5, the surgeon operates a character display/non-display switch, which is one of the switch 11a and switch 11b provided to the foot switch 11, having the functionality for performing instructions to temporarily display or non-display the character display on the monitor 5, thus enabling the information in the character display such as subject ID or image-capturing date for example, serving as information other than the subject image which the image-capturing device 2C has image-captured, to all be temporarily non-displayed, as shown in image 6-2 in FIG. 6. After this, in the state that an image such as that shown in image 6-2 in FIG. 6 is displayed on the monitor 5, the surgeon can operate the character display/non-display switch to cause only a portion of the information in the character display such as subject ID, image-capturing date and so forth, to be non-displayed, as shown in image 6-3 in FIG. 6. Further following, in the state that an image such as that shown in image 6-3 in FIG. 6 is displayed on the monitor 5, the surgeon can operate the character display/non-display switch to cause all of the information in the character display such as subject ID, image-capturing date and so forth, to be displayed again, as shown in image 6-1 in FIG. 6.

Also, in the case of using the endoscope device 1 of the present embodiment, a situation can be conceived wherein an abnormal instruction signal is transmitted to the processor 3, whereby instructions for performing predetermined operations in a normal manner are not made, for example, such as due to an erroneous operation and so forth by the surgeon, external force being continuously applied to one of the four switches belonging to the switch unit 2A of the endoscope 2, and a predetermined operation being performed continuously for longer than the predetermined length of time. The processing performed by the endoscope device 1 of the present embodiment in the case of such a situation occurring will be described with reference to FIG. 7.

First, if the surgeon performs an operation of one of the four switches belonging to the switch unit 2A, the first instruction signal having instructions such as freeze instructions and so forth is transmitted to the CPU 3E of the processor 3, according to the content of the operation (step S1-1 in FIG. 7). For example, in the case that the first instruction is a freeze instruction signal, the CPU 3E controls the various units based on the freeze instruction signal to temporarily stop the transmission of the image signal of the subject image which the image-capturing device 2C has image-captured, and displays a still image of the subject image on the monitor 5 (step S1-2 in FIG. 7). Note that the time wherein the freeze instruction signal is continuously transmitted, which is the display time of the still image, is measured by a counter belonging to the CPU 3E. In the case that the time wherein the freeze instruction signal is continuously transmitted does not exceed a predetermined time $t_1$ serving as the time set in advance as to the CPU 3E by the surgeon operating the terminal device 7 and so forth, and in the case that a noise signal generated by a short and so forth in the wiring within the switch unit 2A is not included in the freeze instruction signal, the CPU 3E determines that a freeze instruction based on the first instruction signal is made normally (step S1-3 in FIG. 7), interrupts the operation based on the freeze instruction signal, and displays the still image of the subject image on the monitor 5 (step S1-2 in FIG. 7).

Also, in the case that the time of the freeze instruction signal being continuously transmitted has exceeded the pre-determined time $t_1$, or in the case that the noise signal generated by a short or so forth in the wiring within the switch unit 2A is included in the freeze instruction signal, the CPU 3E determines that the freeze instruction based on the first instruction signal is not being performed normally (step S1-3 of FIG. 7). After this, until the CPU 3E detects that an instruction signal other than the freeze instruction signal has been transmitted, of second instruction signal which is an instruction signal transmitted by the operation of one of the four switches belonging to the operating panel 3F, the third instruction signal which is an instruction signal transmitted by the operation of one for two switches belonging to the foot switch 11, and the fourth instruction signal which is an instruction signal transmitted by the operation of one of the operating device belonging to the keyboard 8, the receiving awaiting state of these three types of instruction signals is continued (steps S1-4, S1-6, and S1-8 in FIG. 7). Also, when the surgeon operates the operating panel 3F while in this receiving awaiting state, for example, in the case that the release instruction signal is transmitted to the processor 3 as the second instruction signal, the processor 3 stops transmission of the freeze instruction signal with the timing detecting the release instruction signal, and resets the time information measured by the counter belonging to the CPU 3E, as well as records the image signal of the subject image which the image-capturing device 2C has image-captured to the terminal device 7 and so forth as a still image, and completes the release operation (step S1-5 in FIG. 7). Also, in the case that release instruction signal is transmitted to the processor 3 as the third instruction signal or the fourth instruction signal, which in the receiving awaiting state, as described above, the processor 3 stops transmission of the freeze instruction signal with the timing detecting the release instruction signal, and resets the time information measured by the counter belonging to the CPU 3E, as well as records the image signal of the subject image which the image-capturing device 2C has image-captured to the terminal device 7 and so forth as a still image, and completes the release operation (steps S1-7 and S1-9 in FIG. 7).

Note that with the above description, a situation is described wherein the instructions based on the first instruction signal are not performed normally, but for example even in the case wherein the instructions based on the one of the three types of instruction signals other than the first instruction signal are not performed normally, the processor 3 performs processing similar to the processing described above and shown in FIG. 7. That is to say, in the case that the processor 3 according to the present embodiment detects that instructions for character input or the predetermined operations are not performed normally with one of the instruction signals of the first instruction signal, second instruction signal, third instruction signal, and fourth signal, and also detects that instructions for performing an operation other than the character input or the predetermined operations are performed normally, of at least one other instruction signal other than the above-mentioned one instruction signal, the processor 3 stops the transmission of the one instruction signal and also validates the operating content which the other instruction signal instructs.

Also, in the case that one of the first instruction signal, second instruction signal, third instruction signal, and fourth instruction signal have a freeze instruction signal, the processor 3 of the present embodiment can be configured to invalidate arbitrary operation content performed by the operation of one of the switches of the switch unit 2A, operating panel 3F, foot switch 11, and keyboard 8, and to preferentially perform processing to stop the transmission of the freeze instruction signal.

A situation wherein one of the four switches belonging to the switch unit 2A has freeze instruction functionality will be described with reference to FIG. 8.

First, when the surgeon operates one of the four switches belonging to the switch unit 2A, the freeze instruction signal is transmitted as the first instruction signal to the CPU 3E of the processor 3 according to the operation content (step S2-1 in FIG. 8). The CPU 3E controls the various units based on the freeze instruction signal to temporarily stop the transmission of the image signal of the subject image which the image-capturing device 2C has image-captured, and displays the subject image on the monitor 5 as a still image (step S2-2 in FIG. 8). After this, the CPU 3E detects whether or not one of the instruction signals of the first instruction signal, second instruction signal, third instruction signal, and fourth instruction signal have been transmitted, by operation of one of the arbitrary switches of the switch unit 2A, operating panel 3F, foot switch 11, and keyboard 8 (step S2-3 in FIG. 8). In the case that the switch unit 2A and so forth are not operated, and none of the instruction signals of the four types of instructions signals such as the first instruction signal are transmitted, the CPU 3E continues the operation based on the freeze instruction signal, and displays the still image of the subject image on the monitor 5 (step S2-2 in FIG. 8). Also, in the case that the switch unit 2A and so forth are operated, and one of the instruction signals of the four types of instructions signals such as the first instruction signal is detected, the CPU 3E invalidates the operation content based on the instruction signal, and preferentially performs processing to stop the transmission of the freeze instruction signal (step S2-4 in FIG. 8).

Note that there are cases wherein the surgeon will perform processing such as image enhancement and so forth on the still image displayed on the monitor 5, so as to observe the still image displayed on the monitor 5 in detail. In such a case, even if other instruction signals for performing predetermined processing to the still image displayed on the monitor 5 are transmitted in a state wherein the freeze instruction signal is transmitted, the surgeon-can change the settings of the CPU 3E of the processor 3 by operating the terminal device 7 and so forth, so that the processor 3 does not perform processing to stop the transmission of the freeze instruction signal, for example. Examples of the predetermined processing on the still image displayed on the monitor 5 may include enhancing processing for performing image enhancing of the still image displayed on the monitor 5, zoom processing for expanding a portion of the still image displayed on the monitor 5, or character display/non-display processing for temporarily displaying or non-displaying the characters superimposed over and displayed on the still image displayed on the monitor 5. A setting can be made for the CPU 3E of the processor 3 wherein, even if the instruction signal for performing one of the above-described three processes is transmitted in a state wherein the freeze instruction signal is transmitted by the surgeon operating the terminal device 7 and so forth, the processor 3 does not perform processing for stopping transmission of the freeze instruction signal but performs processing based on the instructions.

Also, the processor 3 of the present embodiment may have a configuration wherein, in the case that the processor 3 detects that instructions for performing character input and predetermined operations with one of the instruction signals of the first, third, and fourth instruction signals is continuing for longer than a predetermined time $t_2$, that is to say, in the case that instruction based on the first instruction signal is not performed normally, due to external force based on an erroneous operation and so forth by the surgeon continuously being applied to one of the switch unit 2A, foot switch 11 and keyboard 8, warning notification is performed to the surgeon and so forth by a warning notification unit.

A case wherein one of the two switches belonging to the foot switch 11 has freeze instruction functionality will be described with reference to FIG. 9.

First, when the surgeon operates one of the two switches belonging to the foot switch 11, the freeze instruction signal is transmitted as the third instruction signal to the CPU 3E of the processor 3 according to the operating content (step S3-1 in FIG. 9). The counter belonging to the CPU 3E starts measuring the time that the freeze instruction signal is continuously transmitting with the timing receiving the freeze instruction signal (step S3-2 in FIG. 9). Also, the CPU 3E controls the various units based on the freeze instruction signal to temporarily stop the transmission of the image signal of the subject image which the image-capturing device 2C has image-captured, and displays the subject image on the monitor 5 as a still image (step S3-3 in FIG. 9). In the case that the time which the freeze instruction signal is continuously transmitted does not exceed a predetermined time $t_2$ which is set in advance as to the CPU 3E by the surgeon operating the terminal device 7 and so forth, the CPU 3E determines that freeze instructions are performed normally (step S3-4 in FIG. 9), continues the operation based on the freeze instruction signal, and displays the still image of the subject image to the monitor 5 (step S3-3 in FIG. 9).

Also, in the case that the time which the freeze instruction signal is continuously transmitted exceeds a predetermined time $t_2$ (step S3-4 in FIG. 9), the CPU 3E determines that freeze instructions based on the third instruction signal is not performed normally. After this, the CPU 3E performs control as to the OSD 3D so that a character string is displayed to notify a warning on the image displayed on the monitor 5 serving as a warning notification unit, and also stops the transmission of the freeze instruction signal, and resets the time information measured by the counter belonging to the CPU 3E (step S3-5 in FIG. 9).

Note that the method for notifying a warning are not limited to displaying a character string on the monitor 5, and for example, the CPU 3E can perform control to light an arbitrary LED with the LED unit 3L, or by sounding an arbitrary sound with the speaker 3M.

Also, in the case of using the endoscope device 1 according to the present embodiment, for example, after the power of the endoscope 2 and processor 3 is turned off with one of the four switches belonging to the switch unit 2A of the endoscope 2 remaining in the on state, the power of the endoscope 2 and processor 3 is turned on again. The processing to be performed by the endoscope device 1 according to the present embodiment in the case of such a situation arising will be described with reference to FIG. 10.

When the surgeon turns off the power of the endoscope 2 and processor 3 with one of the four switches belonging to the switch unit 2A of the endoscope 2 remaining in the on state, and subsequently turns on the power of the endoscope 2 and processor 3 again (step S4-1 in FIG. 10), immediately thereafter the first instruction signal having an instruction such as the freeze instructions and so forth is transmitted to the CPU 3E of the processor 3 (step S4-2 in FIG. 10). If the CPU 3E detects that the first instruction signal is transmitted immediately following the power of the endoscope 2 and processor 3 being turned on, the CPU 3E invalidates the operation content instructed by the first instruction signal (step S4-3 FIG. 10). After this, if the CPU 3E detects that an instruction signal other than the first instruction signal is transmitted in the state wherein the first instruction signal continually transmits immediately following the power of the endoscope 2 and processor 3 being turned on (step S4-4 in FIG. 10), the CPU 3E performs operations instructed by the other instruction signal. Also, in the case that the CPU 3E detects that an instruction signal for stopping the transmission of the first instruction signal has been transmitted by the surgeon operating the switch unit 2A and so forth (step S4-6 in FIG. 10), while not detecting that an instruction signal other than the first instruction signal has been transmitted while in the state wherein the first instruction signal is transmitted immediately following the endoscope 2 and processor 3 being turned on (step S4-4 in FIG. 10), the first instruction signal transmission is stopped, and the various instruction signals move into a receiving awaiting state (step S4-7 in FIG. 10). Note that, in the state wherein the first instruction signal is transmitted immediately following the endoscope 2 and processor 3 being turned on, until the CPU 3E detects that one of an instruction signal other than the first instruction signal or an instruction signal for stopping the transmission of the first instruction signal has been transmitted, the state is maintained in which the operation content instructed by the first instruction signal is invalidated.

Note that in the case wherein none of the switches of the switch unit 2A and so forth are turned on, and no instruction signal such as the first instruction signal and so forth is transmitted to the CPU 3E immediately following the power being turned on for the endoscope 2 and processor 3, the CPU 3E determines that startup has been performed normally, and the various instruction signals move into a receiving awaiting state (step S4-7 in FIG. 10).

Note that the foot switch 11 of the present embodiment provides functionality for displaying a setting screen such as that shown in FIG. 3 by the surgeon operating the terminal device 7 and so forth, and for performing instructions such as character display/non-display as to the long-stepping operation which is an operation for pressing one of the switches 11a and 11b only a length of time not exceeding the predetermined time $t_1$ or the predetermined time $t_2$.

Also, in the case that the surgeon has set the functionality for performing instructions to perform operations or processing continuously for a predetermined length of time, such as for moving image recording and so forth, for example, as to the long-stepping operation of one of the switches 11a or 11b, the processor 3 can have a configuration for performing processing to record moving images and so forth only during the time wherein the surgeon presses continuously on one of the switches 11a or 11b, with the time not to exceed the predetermined time $t_1$ or the predetermined time $t_2$.

Also, a configuration may be made wherein, in the case that the endoscope 2 of the present embodiment is changed from a type having a switch unit 2A to a type not having a switch unit 2A, the processor 3 can assign the functions of the four switches belonging to the switch unit 2A to one of the operating panel 3F, the foot switch 11, and the keyboard 8 arbitrarily, based on the content recorded in the endoscope identifier memory 2B and the content set by the surgeon operating the terminal device 7, and so forth.

Further, in the case that the endoscope 2 of the present embodiment is changed from a type using a processor 3 to a type not using a processor 3, and the foot switch 11 is connected to the light-adjusting control unit 4C of the light source device 4, the foot switch 11 may have a configuration such that the light-adjusting control unit 4C detects whether or not the light-adjusting cable 10 is connected to the processor 3, and in the case that the light-adjusting cable 10 is not connected to the processor 3 based on the detection results, the functions of the switches 11a and 11b can be assigned to have functionality such as light amount adjusting instructions, which are functions for transmitting instruction signals to the light source device 4.

Also, with the endoscope device 1 of the present embodiment, a setting can be performed as to the processor 3 wherein an arbitrary sound is sounded from the speaker 3M each time the surgeon operates the terminal device 7 and so forth to operate the four switches belonging to the switch unit 2A and the two switches belonging to the foot switch 11.

The endoscope device 1 according to the present invention can validate operation content for stopping the transmission of the instruction signal for performing an instruction, wherein in the case that instructions for performing predetermined operations are not performed normally, in a state wherein external force is continuously applied to the switch unit 2A and so forth by an erroneous operation of the surgeon, and predetermined operations are continuously performed for longer than a predetermined length of time, and in a state wherein a noise signal is generated by a short and so forth in the wiring within the switch unit 2A. That is to say, the endoscope device 1 according to the present invention can perform control so that in the case of an operation being performed which is not a desired operation, an operation which is not a desired operation is not carried out. Thus, the surgeon can rapidly perform corrections to the erroneous operation of the switch unit 2A and so forth, and as a result, the safety of testing and surgery and so forth can be improved.

Note that the present invention is not limited to the above-described embodiment, and it goes without saying that various modifications and applications can be made without departing from the spirit and scope of the present invention.

What is claimed is:

1. An endoscope device comprising:
    an endoscope; and
    an endoscope control device for performing predetermined control as to the endoscope;
    the endoscope including a first operating unit which is provided as one or a plurality of operating devices having a mechanical configuration, and which transmits a first instruction signal for performing predetermined operations as to the endoscope and the endoscope control device; and
    the endoscope control device including a second operating unit which is provided as one or a plurality of operating devices having a mechanical configuration, and which transmits a second instruction signal for performing predetermined operations as to the endoscope and the endoscope control device; and
    a third operating unit which is provided on the exterior of the endoscope control device as one or a plurality of operating devices having a mechanical configuration, and which transmits a third instruction signal for performing predetermined operations as to the endoscope and the endoscope control device;
    wherein the endoscope control device has a control unit for stopping transmission of an abnormal instruction signal, in the case that any one of the first instruction signal, the second instruction signal, and the third instruction signal is detected to be the abnormal instruction signal, and either of the other instruction signals is detected to be normal, and the control unit validates the operation content which the normal instruction signal instructs.

2. The endoscope device according to claim 1, further comprising:
    a fourth operating unit which is formed of one or a plurality of operating devices having a mechanical configuration, and which transmits a fourth instruction signal in the case of performing a predetermined operation of character input as to the endoscope and the endoscope control device;
    wherein the control unit stops transmission of the abnormal instruction signal, in the case that any one of the first instruction signal, the second instruction signal, the third instruction signal, and the fourth instruction signal is detected to be the abnormal instruction signal, and any of the other instructions signals is detected to be normal, and the control unit validates the operation content which the normal instruction signal instructs.

3. The endoscope device according to claim 2, wherein the endoscope control device has a warning notifying unit for performing warning notification in the event that the endoscope control device detects that one of the first instruction signal, the third instruction signal, and the fourth instruction signal has continuously performed character input or predetermined operations for longer than a predetermined length of time.

4. The endoscope device according to claim 3, wherein the fourth operating unit is a keyboard.

5. The endoscope device according to claim 3, wherein the third operating unit is a foot switch.

6. The endoscope device according to claim 2, further comprising:
    an image-capturing unit for capturing an image of a subject, converting the image-captured image of the subject to an image signal and transmitting this;
    wherein in the event that the control unit detects the one of the first instruction signal, the second instruction signal, the third instruction signal, and the fourth instruction signal has an instruction signal such that instruction is performed to temporarily stop the transmission of the image signal to the image-capturing unit, arbitrary operating content performed after such instruction signal is detected is invalidated within one of the first operating unit, the second operating unit, the third operating unit and the fourth operating unit, and processing for stopping the transmission of the instruction signal is performed preferentially.

7. The endoscope device according to claim 6, wherein the fourth operating unit is a keyboard.

8. The endoscope device according to claim 6, wherein the third operating unit is a foot switch.

9. The endoscope device according to claim 2, wherein the fourth operating unit is a keyboard.

10. The endoscope device according to claim 9, wherein the third operating unit is a foot switch.

11. The endoscope device according to claim 2, wherein the third operating unit is a foot switch.

12. The endoscope device according to claim 1, wherein the third operating unit is a foot switch.

* * * * *